(12) United States Patent
McBrearty et al.

(10) Patent No.: US 7,143,637 B1
(45) Date of Patent: Dec. 5, 2006

(54) DIELECTRIC SLIT DIE FOR IN-LINE MONITORING OF LIQUIDS PROCESSING

(76) Inventors: Michael McBrearty, 705 Yorklyn Rd., Hockessin, DE (US) 19707; Anthony J. Bur, 623 Muriel St., Rockville, MD (US) 20852

( * ) Notice: Subject to any disclaimer, the term of this patent is extended or adjusted under 35 U.S.C. 154(b) by 0 days.

(21) Appl. No.: 10/820,956

(22) Filed: Apr. 8, 2004

Related U.S. Application Data

(60) Provisional application No. 60/461,668, filed on Apr. 11, 2003.

(51) Int. Cl.
*G01N 11/00* (2006.01)

(52) U.S. Cl. .................. 73/53.01; 73/53.04; 73/54.11; 73/54.14

(58) Field of Classification Search ............... 73/53.01, 73/54.04, 54.11, 54.14
See application file for complete search history.

(56) References Cited

U.S. PATENT DOCUMENTS

| | | | | |
|---|---|---|---|---|
| 3,952,577 | A | * | 4/1976 | Hayes et al. .............. 73/54.04 |
| 4,241,602 | A | | 12/1980 | Han et al. ................. 73/54.14 |
| 4,423,371 | A | | 12/1983 | Senturia et al. |
| 4,529,306 | A | | 7/1985 | Kilham et al. |
| 4,710,550 | A | | 12/1987 | Kranbuehl |
| 5,095,278 | A | | 3/1992 | Hendrick |
| 5,208,544 | A | | 5/1993 | McBrearty et al. |
| 5,519,211 | A | | 5/1996 | Bur et al. |
| 5,788,374 | A | | 8/1998 | Bur et al. |

OTHER PUBLICATIONS

S.A. Perusich and M. McBrearty, Polymer Engineering and. Science, vol. 40, p. 214, 2000.

A.J. Bur amd M. McBrearty, Review of Scienfific Instruments, vol. 73, p. 2097, 2002.
D. Kranbuehl et al, Polymer Engineeriong and Science, vol. 29, p. 285, 1989.
D.D. Shepard, Journal of Coatings Technology, vol. 68, p. 99, 1996.
S.D. Senturia et al, Journal of Adhesion, vol. 15, p. 69, 1982.
M.C. Zaretsky et al, IEEE Transactions Electrical Insulation, vol. 24, p. 1159, 1989.
J. Fodor and D.A. Hill, Macromolecules, vol. 25, p. 3511, 1992.
D.R. Day et al, Polymer Engineering and Science, vol. 32, p. 524, 1992.
P.W. Springer et al, Polymer Engineering and Science, vol. 15, p. 583, 1975.
K.B. Migler and A.J. Bur, Polymer Engineering and Science, vol. 38, p. 213, 1998.
A.J. Bur et al, Polymer Engineering and Science, vol. 41, p. 1380, 2001.
A.J. Bur et al, Review of Scientific Instruments, vol. 75, p. 1103, 2004.
D.J. Melotik et al, Thermochimica Acta, vol. 217, p. 251, 1993.
G.M. Maistros et al, Polymer, vol. 33, p. 4470, 1992.

* cited by examiner

*Primary Examiner*—Daniel S. Larkin

(57) ABSTRACT

The dielectric slit die is an instrument that is designed to measure electrical, rheological, ultrasonics, optical and other properties of a flowing liquid. In one application, it is connected to the exit of an extruder, pump or mixing machine that passes liquefied material such as molten plastic, solvents, slurries, colloidal suspensions, and foodstuffs into the sensing region of the slit shaped die. Dielectric sensing is the primary element of the slit die, but in addition to the dielectric sensor, the die contains other sensing devices such as pressure, optical fiber, and ultrasonic sensors that simultaneously yield an array of materials property data. The slit die has a flexible design that permits interchangeability among sensors and sensor positions. The design also allows for the placement of additional sensors and instrumentation ports that expand the potential data package obtained.

10 Claims, 14 Drawing Sheets

DIELECTRIC SLIT DIE FOR IN-LINE MONITORING OF LIQUIDS PROCESSING

CROSS REFERENCE TO RELATED APPLICATIONS

This application claims benefit of Provisional Patent Application Ser. No. 60/461,668 filed Apr. 11, 2003. This application uses the frammis vane disclosed in U.S. Pat. No. 5,208,544 granted May 4, 1993, U.S. Pat. No. 5,519,211 granted May 21, 1996, and U.S. Pat. No. 5,788,374 granted Aug. 4, 1998.

FEDERALLY SPONSORED RESEASRCH

This invention was developed under sponsorship of the National Institute of Standards and Technology, Gaithersburg, Md.

REFERENCE TO SEQUENCE LISTING, A TABLE, OR COMPUTER PROGRAM

Not Applicable

BACKGROUND OF INVENTION

1. Field of Invention

This invention relates to multiple sensor monitoring of material properties of liquids during processing—particularly to the dielectric, optical and ultrasonics properties of molten polymer composites that are processed using an extruder machine.

2. Background of Invention

Many products are formulated by mixing liquid components together and by mixing liquids and solids together. Efficient manufacturing methods usually involve continuous processing whereby components are fed into a process line at one end, are mixed and then are transported by means of pipes and conveyor belts to post processing handling and examination. The properties of the final product are determined by recipes of component content, mixing time, temperature, pressure, chemistry and other process parameters. Often these recipes are complex and need to be monitored continuously in order to maintain product quality. The current practice for many processes is to examine product quality after the product has been made. In many cases, post-processing examination takes days or weeks to complete. On-line, real-time processing will eliminate the knowledge delay about the process, allow for immediate correction of process problems and be a sentry for the maintaining process integrity and product quality.

On-line process sensors of many types have been developed. These include ultrasonics, optics, rheological, and dielectric sensors. Applications of these sensors have involved installations of a single sensor with a focus on one material property. Multifunctional sensing with several sensors installed in an on-line chamber with multiple sensor ports is not currently practiced. For processing of complex liquids, such as polymer composites, foodstuffs, and mixtures in slurries, multiple sensing is needed because a single sensor, such as temperature or pressure, does not provide enough information to assess the condition and quality of the product. Each sensor has its assets and limitations whereas multiple sensors provide a collection of data, which, when integrated together, potentially yield a critical level of information.

This invention not only addresses the need for more information about the processes and the material being processed, it also presents an improvement of the dielectric sensor design of McBrearty and Perusich, U.S. Pat. No. 5,208,544. The dielectric sensor of this invention is of the interdigitating electrode type, a concept that was developed by Senturia et al., U.S. Pat. No. 4,423,371, and subsequently commercialized by Micromet. Kranbuehl, U.S. Pat. No. 4,710,550, refined the measuring technique and the sensor so that the real and imaginary parts of the dielectric constant $\epsilon'$ and $\epsilon''$ could be measured using a network analyzer. The Senturia et al. and Kranbuehl sensors were used primarily at low temperatures and in benign environments and are not suitable for measuring abrasive, molten plastics processed under flow at high temperatures and pressures. High temperature dielectric monitoring of highly viscous molten plastic was accomplished by McBrearty and Perusich who used a ceramic ring with interdigitating electrodes deposited and fired onto the inside of the ring. Dielectric properties of fluids flowing through the ring are measured. The design of the McBrearty and Perusich cell consists of the ceramic ring sandwiched between high temperature gaskets that are bolted between two stainless steel cylinders, and the entire housing is wrapped with temperature controlled heater bands. When connected to a process extruder or pump, the gaskets provide a leak-proof, flow-through cell for processing liquids under pressure.

The problem with the ceramic ring design is the limited extent to which the fringe field can interrogate the flowing liquid. For example, a ring with 12.7 mm inside diameter and having electrode separation $\lambda=0.5$ mm can interrogate only a thin shell near the electrodes that amounts to 15% of the cross section of the liquid flow stream. This is because the electric fringing field from the interdigitating electrodes decreases exponentially in intensity from the electrode surface with a characteristic length of $\lambda/3$. If $\lambda$ is made larger in order to extend the fringe field, the sensitivity of the cell is diminished because of decreased capacitance. Sampling only 15% of the processed liquid is not satisfactory because it may not be representative of the total bulk properties.

Other problems with the ceramic ring design are the gaskets that are placed on either side of the ceramic ring in order to seal the unit and protect it from leaks. When processing polymers, these gaskets must perform at high temperatures for long periods of time. They are made of a specialty compound and they are expensive to replace as is needed during the normal course of operation.

It is the purpose of this invention to provide a common platform in a process line on which multiple sensors can be installed. Also, an integral part of this invention is an improved dielectric sensor. The dielectric sensor of this invention retains the robustness of the ceramic substrate used by McBrearty and Perusich while adding flexibility and new capabilities. The electroded ceramic substrate is used in an innovative slit design that incorporates complementary sensors and slit geometry while eliminating gaskets. Also, the design permits interchangeable ceramic substrates with different electrode patterns and electrode separation $\lambda$. The common platform is a slit through which processed liquids flow. The slit is made long enough to accommodate the sensors that access the liquid flowing therein. The slit defines a sample chamber of constant volume that is continuously being replenished by new material as the liquid flows into and out of the slit.

The advantages of this invention are: (a) the slit configuration that confines the flowing liquid to a thin ribbon for which a significant fraction of its cross section is intersected by the fringing electric field lines; (b) the slit configuration that defines a sample chamber of fixed dimensions along which other sensors can be positioned; (c) the slit is the geometry of a slit die rheometer so that with knowledge of the pressure drop across the length of the slit and the volume flow rate, the viscosity of the material can be determined; (d) the simplicity of design eliminates gaskets and adhesives in the assembly; (e) the interchangeability of parts permits the use of different electrode patterns to measure near surface, bulk and orientation effects in the dielectric phenomena; (f) the flexibility of design permits the addition of new sensors and sensor port sectors in line with the dielectric slit die; and (g) because the slit shape confines fluid flow by applying shear stress to the fluid, this design decreases the transition time for flushing the slit volume of the old liquid when making a change in the process from one composition to another.

This invention fulfills a need in liquids processing that will produce improved product quality and productivity. Commercial applications of this device cut across many industries in which liquids are mixed and processed according to a formula that must be continually monitored in order to maintain product quality. Plastics, paints, cosmetics, chemicals, pharmaceuticals, building products, food and beverage industries can utilize this invention because it can be used to determine mixture ratios and important material properties, such as electrical, optical, and rheological properties. Knowledge of these materials properties can be used to predict product performance and to understand and control the process.

BREIF SUMMARY

The dielectric slit die is a multifunctional instrument that is used to measure the materials properties of liquid materials while they are being processed in a continuous flow stream. In one application, it is connected to the exit of an extruder, pump or mixing machine that passes liquefied material, such as molten plastic, solvents, slurries, colloidal suspensions, and foodstuffs, into the sensing region of the slit shaped die. The dielectric slit die has a steel housing that contains instrument ports for a plurality of sensors to access the flowing liquid. In this design the slit forms a platform of uniform dimensions upon which multiple sensors can be mounted. Dielectric sensing is the primary sensor of the slit die, but in addition, the die contains other sensing devices, such as pressure, optical fiber, and ultrasonic sensors, that simultaneously yield an array of material property data. The slit die has a flexible design that permits interchangeability among sensors and sensor positions and permits changes in the slit dimensions. The design also allows for the placement of additional sensors and instrumentation ports that expand the potential data package obtained. A plurality of sensors comprising a dielectric sensor, a temperature sensor, a pressure sensor, an optical sensor, an ultrasonics sensor and any sensor that can be used to measure the material properties of the flowing liquid are candidate measuring tools.

The dielectric sensor is an interdigitating electrode type where the interdigitated electrodes are deposited on a flat ceramic substrate that forms one surface of the slit. When a voltage is applied to the electrodes, a fringing electric field reaches into the liquid flow stream as it traverses the slit. By measuring the in-phase and out-of-phase current flowing in the liquid, it is possible to calculate the dielectric permittivity and the dielectric loss of the processed liquid. The optical sensor consists of a sensor bolt that can be inserted into the standard half-inch instrument port that exists on many processing machines. The sensor bolt is a sleeve with a sapphire window at its end that can receive an optical fiber for transmitting light through the sapphire window. When inserted into the instrument port, the sapphire window sits flush with the surface of the slit and optical sensing of the flowing liquid is achieved. Light reflected back from the opposite wall of the slit and into collection optical fibers is used to measure optical transmission. When a fluorescent dye is mixed with the flowing liquid, a spectrum can be obtained by connecting the collection optical fibers to a monochromator. A pressure sensor at an upstream position in the slit will yield the pressure drop in the slit from which the viscosity of the liquid can be obtained when the flow rate is known. The objective of using multiple sensors is to obtain simultaneous information about the processed liquid so that the process can be controlled and material specifications can be maintained. The dielectric slit die is designed as a robust manufacturing unit that can be used for processing abrasive polymer composites at high process temperatures and pressures.

DRAWINGS

Figure 8A:
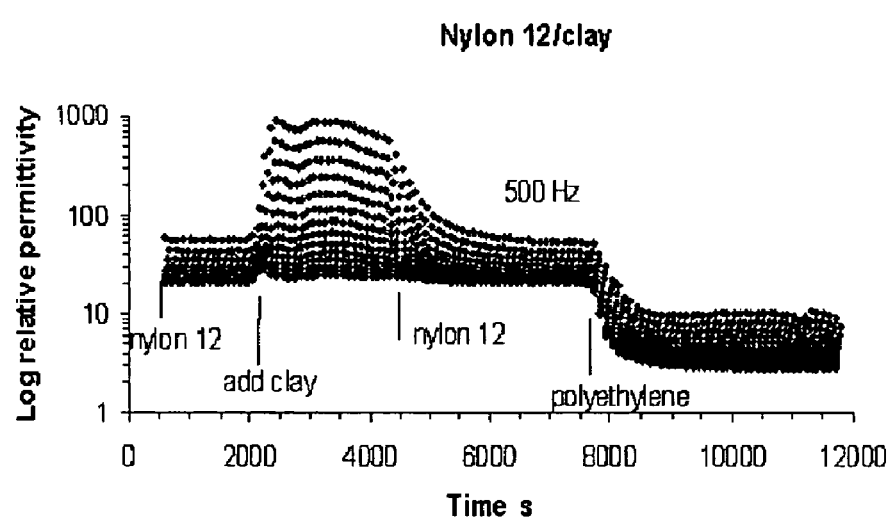

FIG. 8a shows the relative permittivity for the nylon 12, nylon 12 compounded with clay filler, and polyethylene versus time at 15 frequencies between 500 Hz and $10^5$ Hz. The materials were extruded at 195° C.

Figure 8B:
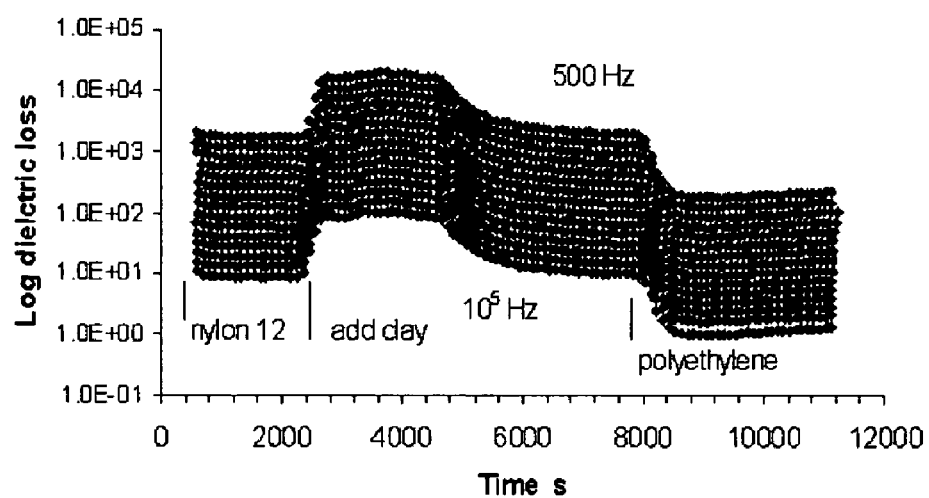

FIG. 8b shows dielectric loss for the nylon 12, nylon 12 compounded with clay filler, and polyethylene versus time at 15 frequencies between 500 Hz and $10^5$ Hz. The materials were extruded at 195° C.

Figure 9A:
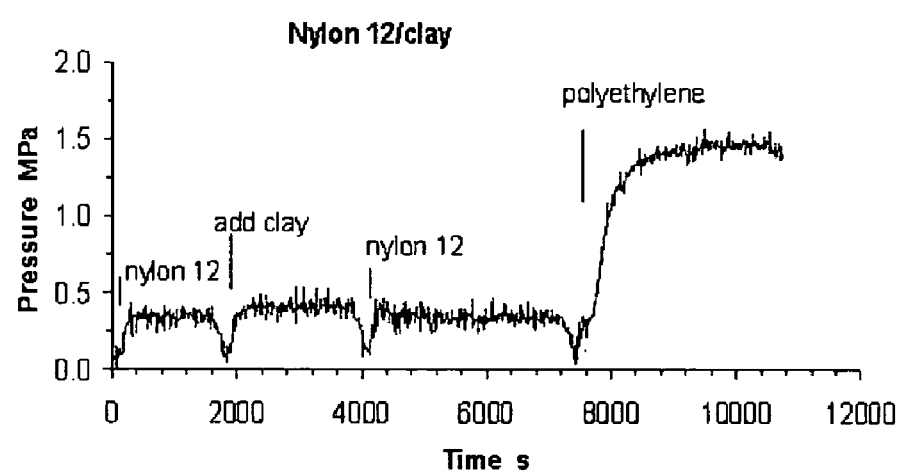

FIG. 9a shows the pressure drop along the slit versus time for extrusion of nylon 12, nylon 12 compounded with clay filler, and polyethylene. The data are from the same experiment as FIGS. 8a, 8b, and 9b.

Figure 9B:
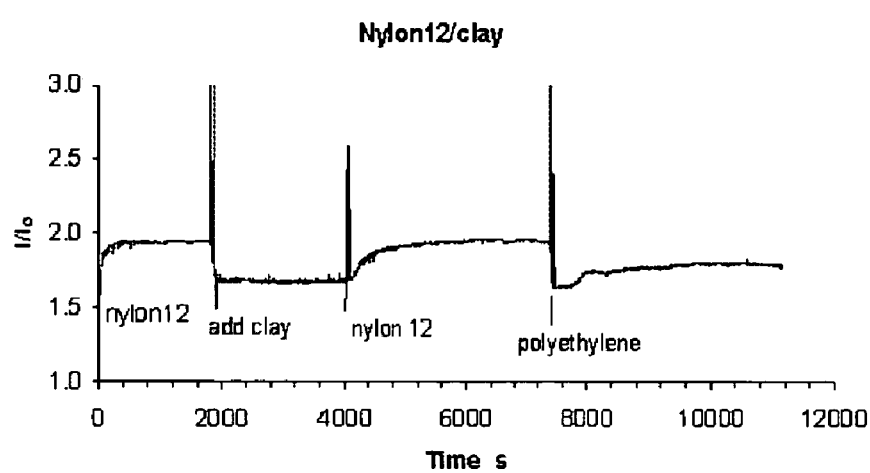

FIG. 9b shows light transmission versus time for extrusion of nylon 12, nylon 12 compounded with clay filler, and polyethylene. The data are from the same experiment as FIGS. 8a, and 8b, and 9a.

Figure 10:
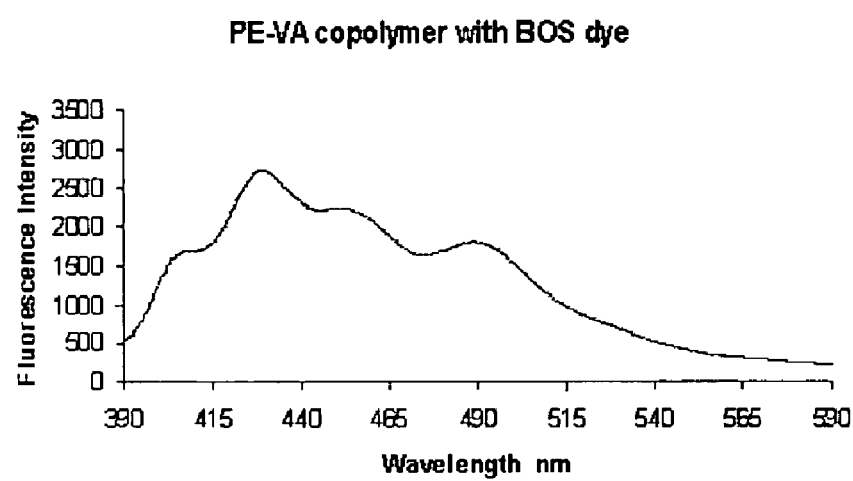

FIG. 10 is a plot of intensity versus wavelength for a fluorescent dye benzoxazolyl stilbene that was compounded with polyethylene-vinyl acetate copolymer. The dye was excited with 365 nm wavelength light. The material was extruded at 150° C.

DETAILED DESCRIPTION OF PATENT

The dielectric slit die 1 is a real-time process monitoring device for measuring material properties of flowing liquids. It is designed to attach to the exit of an extruder or pump that forces a processed liquid through a slit channel under pressure. The slit channel 2, with dimensions of 2 mm high by 2.8 cm wide by approximately 17 cm in length, defines a constant geometry sample cell in which the processed material is examined by on-line sensing devices. The primary sensor in the channel is the dielectric sensor consisting of interdigitated electrodes 3 that are deposited onto a ceramic substrate 4. The current configuration of this invention includes pressure, optical fiber, and ultrasonic sensors, but its flexible design allows for the addition of new sensors and instrumentation ports, and permits the interchange of sensors to different positions in the slit channel.

Figure 1A:
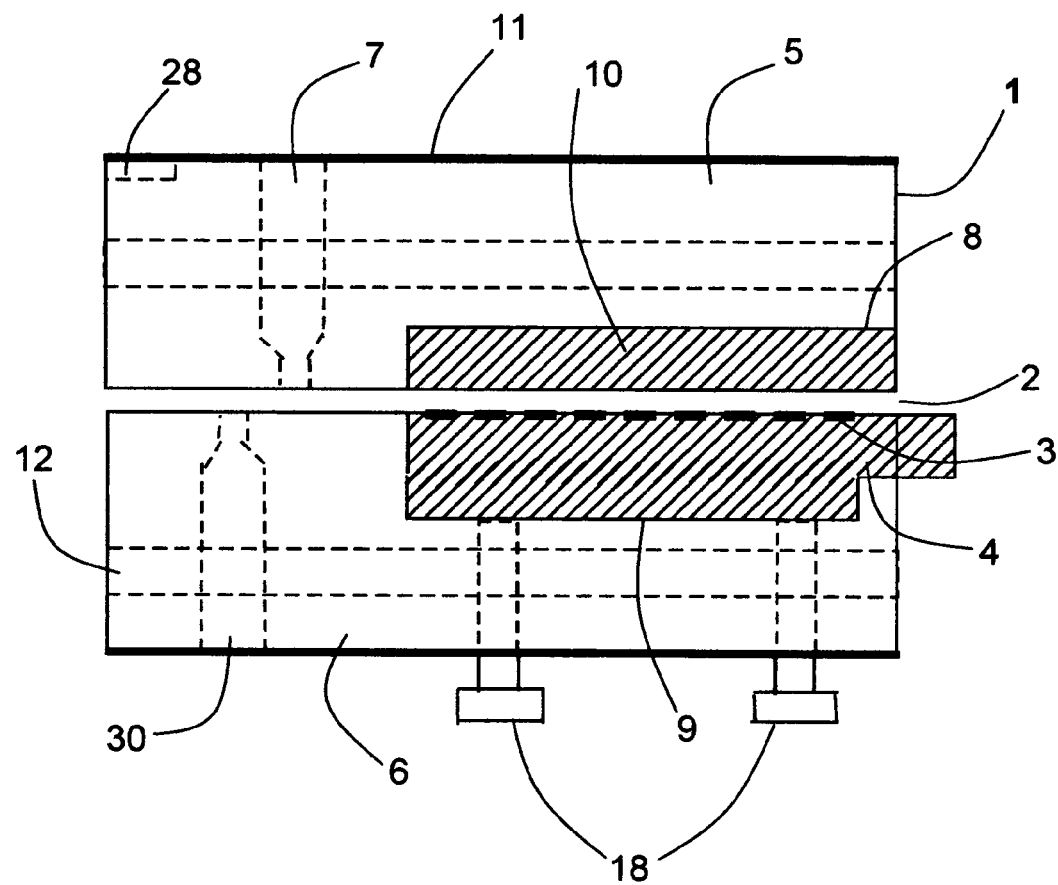
FIG. 1a is a side view of the dielectric slit die showing the sensor ports and the ceramic substrates of the dielectric sensor.
Figure 1B:
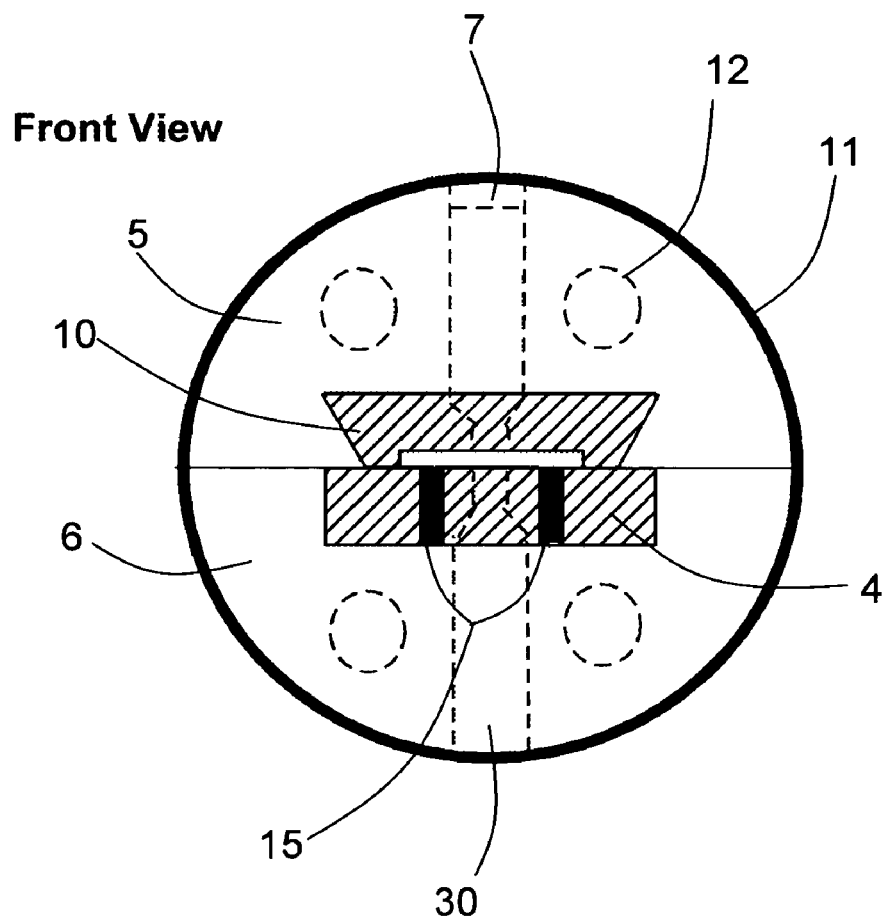
FIG. 1b is a front view of the dielectric slit die.

A schematic diagram of the dielectric slit die is shown in FIGS. 1a and 1b. All sensors in the slit die are contained in a cylindrical stainless steel housing that consists of upper 5 and lower 6 halves. It contains threaded instrumentation ports 7 and 30 of the standard half-inch by twenty threads-per-inch type in addition to two cut out chambers 8 and 9 for ceramic in-lays that are used for dielectric sensing. The ceramic piece on the bottom 4 is high purity alumina onto which platinum electrodes have been deposited and fired in an interdigitating pattern 3. The ceramic 10 in the top half is made from a machinable ceramic, has a trapezoidal cross section, and contains a cutout of the slit channel 2 that is 2 mm deep by 2.8 cm wide extending over the length of the piece that is approximately 11 cm. The trapezoidal cross section serves to hold the piece into place in the top half stainless steel piece 5. The entire slit die unit, which is 12.7 cm in diameter by approximately 17 cm long, is wrapped with temperature controlled heater bands 11.

Figure 2:
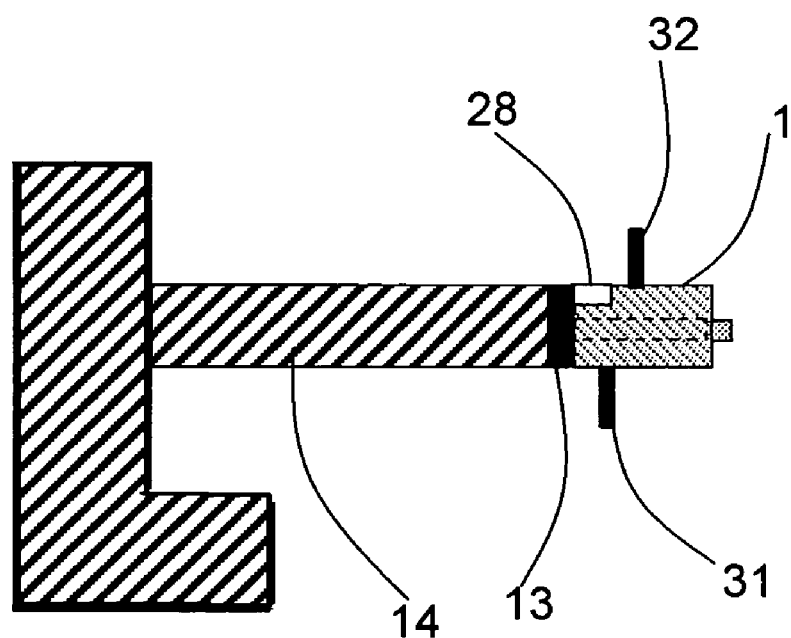
FIG. 2 shows the dielectric slit die attached to an extrusion machine.

A typical application is depicted in FIG. 2 where the dielectric slit die 1 has been attached to the end of a plastics extrusion machine 14 using four bolts that extend through holes 12 in the steel housing, as shown in FIGS. 1a and 1b, to an adapter plate 13 at the end of the extruder 14. In this case, the properties of the extruded plastic are measured in real-time at the temperature of processing. In addition to the dielectric sensor, two other sensors 31 and 32 are shown in the setup of FIG. 2, and additional sensor ports can be machined into the stainless steel housing. Real-time materials property data can be used for quality control and as measurement values that are utilized in a feedback loop to control the process. All of the active sensors in the slit die have their corresponding detector that is coupled to a computer for data acquisition. For the dielectric measurement, various methods to detect the real and imaginary parts of the dielectric constant can be used. Such methods include a lock-in amplifier to detect amplitude and phase of the current that results from the application of a voltage across the electrodes, or a network analyzer, or a dielectric bridge, or a dielectric spectrometer.

Figure 3:
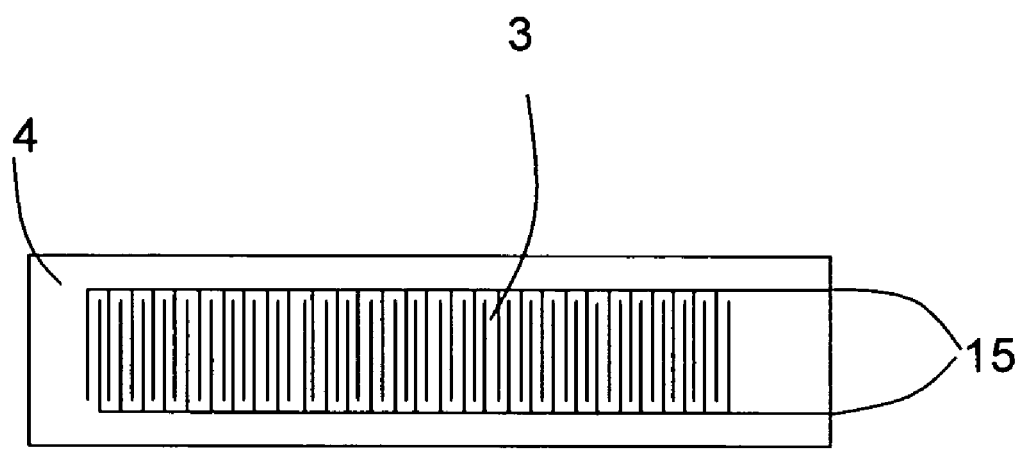
FIG. 3 shows the basic interdigitating electrode arrangement that is deposited on a ceramic substrate.

The electrodes of the dielectric sensor are deposited onto an alumina ceramic substrate 4 in an interdigitating pattern of finger electrodes 3. Two sets of finger electrodes are interwoven to create the sensor, as shown in FIG. 3. Each set of fingers is connected to a lead electrode 15, and when an alternating voltage is applied to the electrodes, an electric field fringes between neighboring finger electrodes and extends not only through the alumina ceramic 4, but also into the liquid media flowing above the surface. In practice, the lock-in amplifier is used to measure the dielectric properties of the electroded alumina piece as a function of temperature and frequency when the slit die is empty. These data are stored in a calibration file in the computer. With liquid flowing through the slit 2 and a voltage applied to the electrodes 3, the value and phase of the resultant current is measured. By subtracting out the current through the alumina, the relative permittivity $\epsilon'$ and dielectric loss $\epsilon''$ of the liquid media can be determined. The data are recorded as complex dielectric permittivity $\epsilon^*$ where $\epsilon^* = \epsilon' - i\epsilon''$. The measurement procedure was developed by McBrearty and Perusich.

Because the fringing field is strongest near the surface, the sensitivity of the dielectric sensor is biased toward the surface. The spatial extension of the electric field into the media under investigation is determined by the spacing between the electrode fingers. The field decreases in strength exponentially with distance from the surface with a characteristic length $\lambda/3$ where $\lambda$ is the distance between neighboring electrodes. To measure dielectric properties near the surface, a small value of $\lambda$ is needed. Conversely, to allow the field to reach into the bulk of the flowing media, a relatively large value of $\lambda$ is needed. Thus, if $\lambda$ is 1 mm, then the field strength decays with a characteristic dimension 0.33 mm and the farthest extension of the field is approximately 1.5 mm. To extend the field farther into the flowing liquid by making $\lambda$ larger has its limits because, as $\lambda$ increases, the capacitance of the cell decreases compromising the sensitivity of the sensor. An appropriate balance between sensitivity and the spatial extent of the field must be taken in account when designing the electrode pattern. The slit height is set to be larger than the outward reach of the fringing field, so that the dielectric properties of the ceramic piece 10 in the upper half of the slit die are not a factor in the measurement. In order to sample a significant fraction of the cross section of the flowing liquid, the current embodiment of the slit die is designed with a 2 mm slit height and $\lambda = 0.5$ mm, but these dimensions can be changed by cutting the slit height in the upper ceramic piece to a different size and using a different electrode pattern.

Figure 4A:
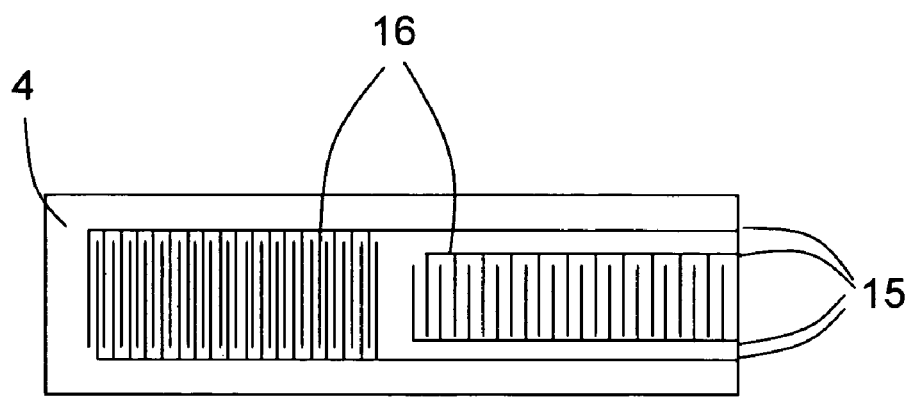
FIG. 4a shows two interdigitating electrode patterns deposited on the same ceramic substrate. The two patterns have different electrode separations that create fringing fields closer and farther from the surface of the ceramic.
Figure 4B:
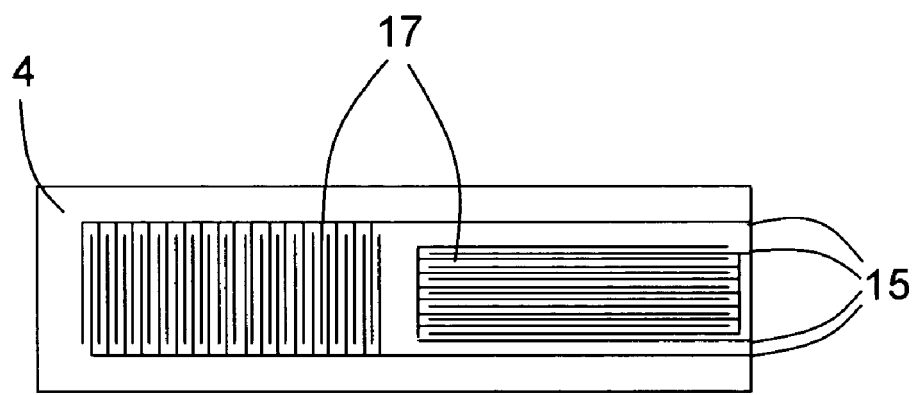
FIG. 4b shows two interdigitating electrode patterns that are oriented at 90° with respect to each other creating fringing electric fields that are oriented at 90° with respect to each other.

The design of the dielectric slit die permits interchangeable ceramic substrates with different electrode patterns and electrode separation $\lambda$. The electrodes are deposited and fired on a flat surface making it convenient for depositing different electrode patterns. For example, the dual electrode patterns 16 shown in FIG. 4a can be used to measure simultaneously near surface dielectric properties as well as bulk properties because the two patterns have significantly different electrode separation. FIG. 4b displays patterns 17 oriented at 90° to each other for the purpose of investigating orientation effects in a liquid of high viscosity undergoing shear flow. The alumina ceramic 4 is positioned in a well that has been machined into the bottom half stainless piece 6 and is held mechanically in place by clamping top and bottom halves together. No epoxy or other adhesive is needed. To change ceramic substrates, the alumina block is removed from its well using the lifting bolts 18, as shown in FIG. 1a, on the bottom of the housing to push the block out of the well. It can be replaced with electroded alumina substrates with different electrode patterns. Likewise, the ceramic piece 10 with the cut-out slit in the top half of the sensor can be interchanged with pieces having different slit sizes.

The slit configuration accomplishes three objectives: first, it confines the flowing liquid to a thin ribbon for which a significant fraction of its cross section is intersected by the fringing electric field lines; second, the slit defines a sample chamber of fixed dimensions along which other sensors can be positioned; and third, it is the geometry of a slit die rheometer so that with knowledge of the pressure drop across the length of the slit and the volume flow rate, the viscosity of the material can be determined. The pressure transducer is positioned upstream from the dielectric sensor and yields the value of the pressure drop along the axial length of the slit 2.

Figure 5:
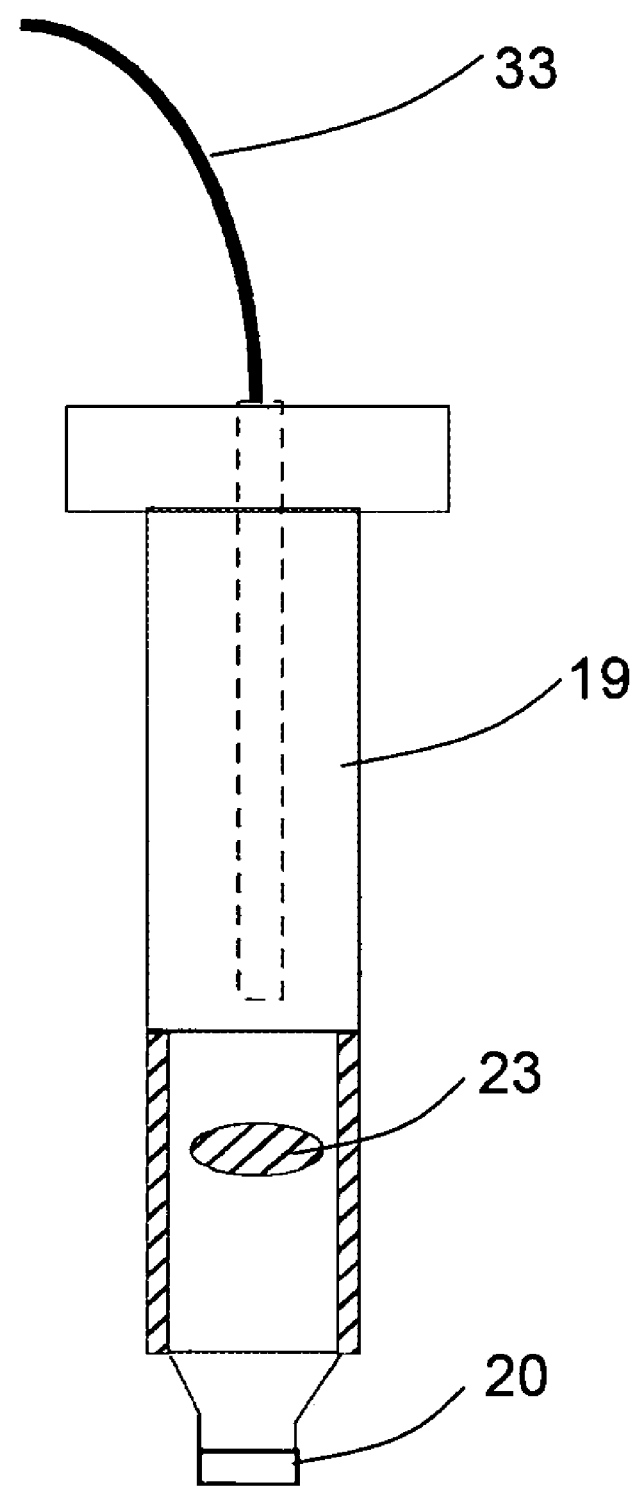
FIG. 5 is a drawing of an optical sensor bolt that has been machined to receive an optical fiber, a focusing lens and a sapphire window at its end.
Figure 6:
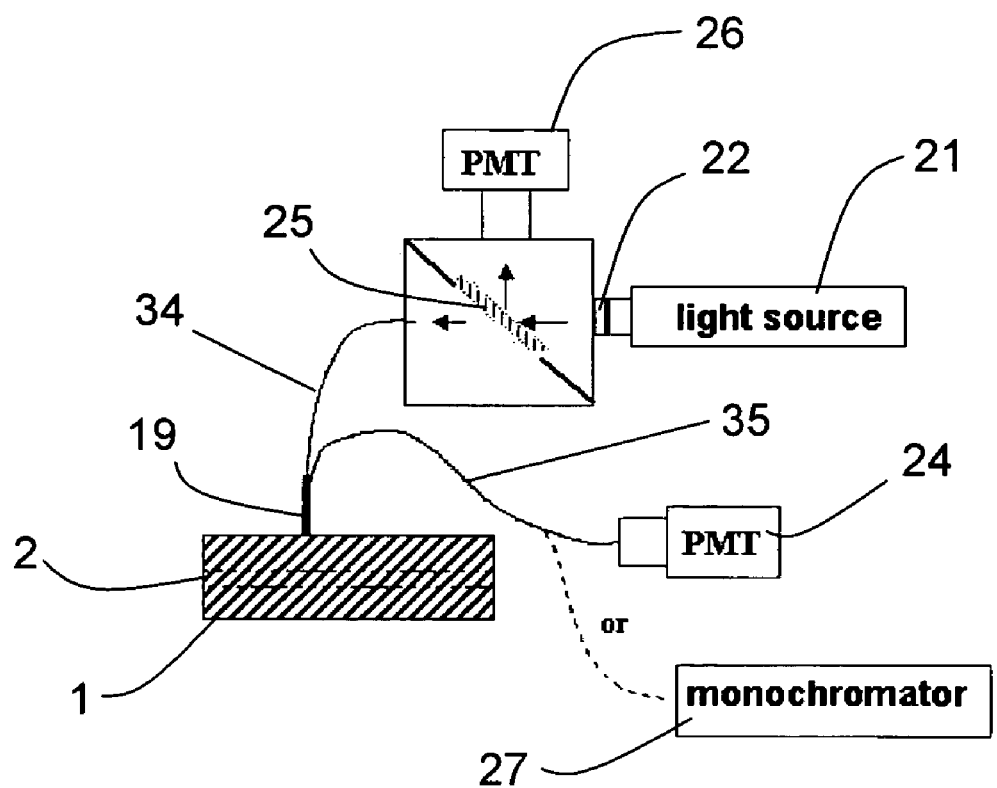
FIG. 6 is a diagram of the optics setup used for measuring light transmission and fluorescence. PMT refers to photomultiplier tube.

The optics sensor, shown in FIG. 5, is situated upstream from the dielectric sensor in the stainless steel portion of the slit die. It consists of a bundle of seven 200 µm core optical fibers 33 that are placed into a sleeved half-inch sensor bolt 19 with a sapphire window 20 at its end. It operates in the reflection mode, i.e. one of the fibers 34, shown in FIG. 6, transmits light from the light source 21 (that has been confined to a narrow wavelength band by a filter 22) through a focusing lens 23, the sapphire window 20, the flowing liquid, reflects off the far stainless steel surface, and reverses its path through the material, sapphire window 20 and lens 23. The reflected light is collected by the other six fibers 35 and is transmitted to the photomultiplier (PMT) detector 24 as shown in FIG. 6. The intensity of the light source 21 is monitored using a beamsplitter 25 that sends a source sampling beam to another photomultiplier (PMT) 26. The ratio of the two light intensities is used to monitor the light transmission through the liquid. In this manner fluctuations in light source intensity are cancelled out. The light sensor can also be used for fluorescence monitoring where the single optical fiber transmits the excitation light to the flowing liquid, and fluorescence collected by the six fibers is transmitted to a monochromator 27. For fluorescence detection, the monochromator substitutes for the PMT 24 in FIG. 6.

A machined flat at the back end of the slit die is reserved for an ultrasonics sensor 28. In this position, the ultrasonic sensor functions in a manner similar to the optical sensor, i.e. in the reflection mode. A transducer placed on the flat area transmits an ultrasonic wave through the stainless steel housing, through the material under investigation, reflecting off the far stainless steel wall, reversing its direction, taking a second pass through the material and returning through the stainless steel to the transducer that acts as both transmitter and detector. Using standard ultrasonics detection equipment, both the attenuation of the ultrasonic energy and the velocity of the wave in the examined material can be measured. Ultrasonics velocity is related to the bulk modulus of the material and the attenuation of ultrasonics energy is related to absorption and scattering of the ultrasonics wave.

Figure 7:
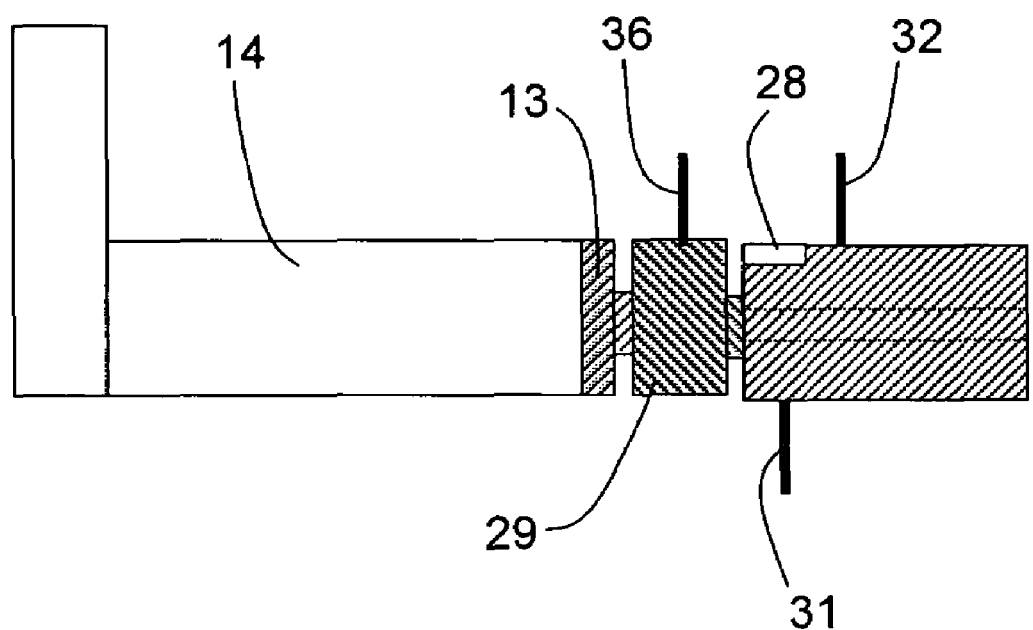
FIG. 7 shows the position of the additional sensor sector that can be added to the sensor train in order to employ more sensors.

As shown in FIG. 7, additional instrumentation port sectors 29 can be added in-line with the slit die 1, sandwiched between the extruder 14 with the adapter plate 13 and the slit die. These sectors can have standard half-inch instrumentation ports or have a custom port configuration for special sensors 36, such as opposing optical windows, that are used for IR and UV spectroscopy. The instrument port sectors can be placed in service as the need for new data arises.

Example 1

To demonstrate the operation of the dielectric slit die, we show the results, in FIG. 8, of single screw compounding of nylon 12 with 4% smectite clay. FIGS. 8a and 8b show real-time data for extrusion of nylon 12 (neat) and for nylon 12 compounded with 4% clay. Compounding was carried out at 195° C. Relative permittivity and conductivity are plotted versus time for fifteen different frequencies ranging from 500 Hz to 100 kHz. At t=400 s, the neat polymer entered the electrode region of the dielectric sensor and was extruded for approximately 1500 s, at which time resin pellets mixed with 4% mass fraction of clay were added to the feeder. Permittivity and conductivity began to increase as the mixture filled the slit region, and after significant transition time, the data reached a plateau value. The transition is associated with time it takes the clay/polymer mixture to completely fill the sensing region, particularly at the surface near the electrodes. At t=4200 s, the neat resin was again introduced and relative permittivity values returned to their original values.

The difference in relative permittivity at low frequency (500 Hz) and high frequency (105 Hz) is called the dielectric dispersion. We see that the dispersion for the clay/polymer nanocomposite is considerably larger than that for the neat polymer. This is because clay particles introduce ionic species into the resin mixture that contribute to conductivity and polarization over and above that which is present in the neat resin.

FIGS. 9a and 9b show pressure and optical signals as a function of time corresponding to the time scale of FIGS. 8a and 8b. Steady state conditions prevail after the transitions are complete. The optical transmission data are expressed as $I/I_o$ where I is the intensity of light transmitted through the extruded resin in the slit and $I_o$ is the intensity of the light source. The optical data show attenuation of the optical beam as it transmits through the neat and clay filled nylon. These data can be correlated with the volume fraction and microstructure of clay in nylon 12. Steady state pressure in conjunction with the volume flow rate can be use to calculate an apparent viscosity using equations for liquid flow through a slit die. In this case apparent viscosity values of 139 Pa·s and 164 Pa·s were obtained for the neat and clay filled nylon 12 at 195° C., respectively.

Example 2

Real-time fluorescence monitoring is illustrated in FIG. 10. Here, polyethylene vinyl acetate copolymer, containing a low concentration of the fluorescent dye benzoxazolyl stilbene, was extruded through the slit and the fluorescence spectrum was detected using a monochromator as illustrated in FIG. 6. The spectra can be used to determine machine residence time and resin temperature.

We claim:

1. An apparatus having a plurality of sensors that monitor material properties of a liquid medium, said apparatus comprising:

a flow channel of predetermined shape and dimensions, said flow channel being a path for a flow of a liquid medium, whereby said liquid medium is contiguous with a surface of said flow channel;

a metal housing of predetermined shape and dimensions surrounding said flow channel, said metal housing comprising an upper half and a lower half that are contiguous;

a first plurality of sensor ports in said metal housing for providing a plurality of sensors access to said liquid medium;

a first recess of predetermined shape and dimensions in said lower half for receiving a first ceramic block of predetermined shape and size thereby creating an exposed planar surface of said first ceramic block that is contiguous with said flow channel;

a second recess of predetermined shape and dimensions in said upper half for receiving a second ceramic block of predetermined shape and size thereby creating an exposed surface of said second ceramic block that is contiguous with said flow channel, said second ceramic block disposed opposite and facing said first ceramic block;

a first lead electrode that is disposed on said exposed planar surface of said first ceramic block and a second lead electrode that is disposed on said exposed planar surface of said first ceramic block, said second lead electrode does not touch said first lead electrode;

a first multitude of finger electrodes of predetermined shape and dimensions, said first multitude of finger electrodes disposed on said exposed planar surface of said first ceramic block so that no finger electrode touches any other said finger electrode and so that said first multitude of finger electrodes is contiguous with said first lead electrode;

a second multitude of finger electrodes of predetermined shape and dimensions disposed on said exposed planar surface of said first ceramic block so that no said finger electrode touches any other said finger electrode and said second multitude of finger electrodes is contiguous with said second lead electrode, said first multitude of finger electrodes and said second multitude of finger electrodes are interleaved and alternately disposed means for forming interdigitating electrodes disposed on said exposed planar surface of said first ceramic block so that said first multitude of finger electrodes and said second multitude of finger electrodes are not touching;

a first detector means for measuring electrical admittance of said interdigitating electrodes, said detector means connected across said first lead electrode and said second lead electrode;

an interchange channel of predetermined shape and dimensions that is aligned with and contiguous with said flow channel and is sandwiched between said flow channel and machine means for pumping said liquid medium into said interchange channel, said interchange channel aligned with said machine means, whereby said interchange flow channel directs said flow of said liquid medium into said flow channel;

a metal adapter plate of predetermined shape and dimensions surrounding said interchange channel, said metal adapter plate sandwiched between said metal housing and said machine means for pumping said liquid medium, said metal adapter plate contiguous with said metal housing and said machine means for pumping said liquid medium;

a first means for controlling temperature of said metal housing and said metal adapter plate and a plurality of detectors means for measuring responses from said plurality of sensors.

2. An apparatus in accordance with claim 1, wherein said flow channel has a cross sectional shape of a slit with a width that is greater than ten times a height of the flow channel.

3. An apparatus in accordance with claim 1, wherein a length of said flow channel is long enough to accommodate said plurality of sensor ports in said metal housing for forming a slit sample chamber with fixed height along the entire length of said flow channel.

4. An apparatus in accordance with claim 1, wherein said plurality of sensors is selected from a group comprising at least one of the following a pressure sensor, and a temperature sensor, and an electric sensor, and a dielectric sensor, and an ultrasonic sensor, and an optical sensors and a magnetic sensors and a mechanical sensor, and a radiation sensor, and an ultraviolet absorption sensors and an infrared absorption sensor, and a microscopy image sensor.

5. An apparatus in accordance with claim 1, wherein said finger electrodes of said interdigitating electrodes have an identical predetermined shape and dimension.

6. An apparatus in accordance with claim 5, wherein each said finger electrode is separated from its nearest neighbor by a predetermined identical distance so as to control a spatial definition of a fringing electric field inside said flow channel.

7. An apparatus in accordance with claim 6, wherein said interdigitating electrodes are oriented at a predetermined angle with respect to a flow direction of said liquid medium.

8. An apparatus in accordance with claim 6, wherein first interdigitating electrodes of first predetermined shape and dimension and angle with respect to said flow direction and second interdigitating electrodes of second predetermined shape and dimension and angle with respect to said flow direction are disposed on said exposed planar surface of said first ceramic block for producing a first fringing electric field and a second fringing electric field so that said first fringing electric field and said second fringing electric field have different directions and spatial definition.

9. An apparatus in accordance with claim 1, further including a lifting bolt means for removing said first ceramic block from said first recess in said lower half.

10. An apparatus in accordance with claim 1, further including an additional instrument sensor sector comprising a second plurality of sensor ports, said additional instrument sensor sector sandwiched between and contiguous with said metal adapter plate and said metal housing said additional instrument sensor sector surrounding a sector channel that is aligned with said flow channel and said interchange flow channel.

* * * * *